United States Patent [19]

Walters et al.

[11] 4,030,493
[45] June 21, 1977

[54] RESPIRATORY MOUTHPIECE

[75] Inventors: William T. Walters; Marvin D. Parlette, Jr., both of Toledo, Ohio

[73] Assignee: Conceptual Products, Inc., Toledo, Ohio

[22] Filed: June 18, 1976

[21] Appl. No.: 697,410

[52] U.S. Cl. .............................. 128/147; 128/208
[51] Int. Cl.² ...................................... A61M 16/00
[58] Field of Search ............ 128/147, 146.7, 146 R, 128/145 A, 145 R, 145.8, 145.7, 145.5, 142 R, 141 R, 140 R, 188, 198, 201, 208, 351, 136

[56] References Cited
UNITED STATES PATENTS

| 2,857,911 | 10/1958 | Bennett | 128/147 |
| 3,079,916 | 3/1963 | Marsden | 128/147 |
| 3,303,845 | 2/1967 | Detmer | 128/147 |

*Primary Examiner*—Robert W. Michell
*Assistant Examiner*—Henry J. Recla
*Attorney, Agent, or Firm*—Carl G. Staelin

[57] ABSTRACT

A respiratory mouthpiece for a positive pressure breathing apparatus made as an integral flexible elastomer molding in an oval concave shape having a ridge along the inner periphery to provide a seal against the outer surfaces of the mouth when pressed against the face and an opening in the center of the mouthpiece defined by a tube to fit over a mouthpiece holder of a breathing apparatus.

5 Claims, 4 Drawing Figures

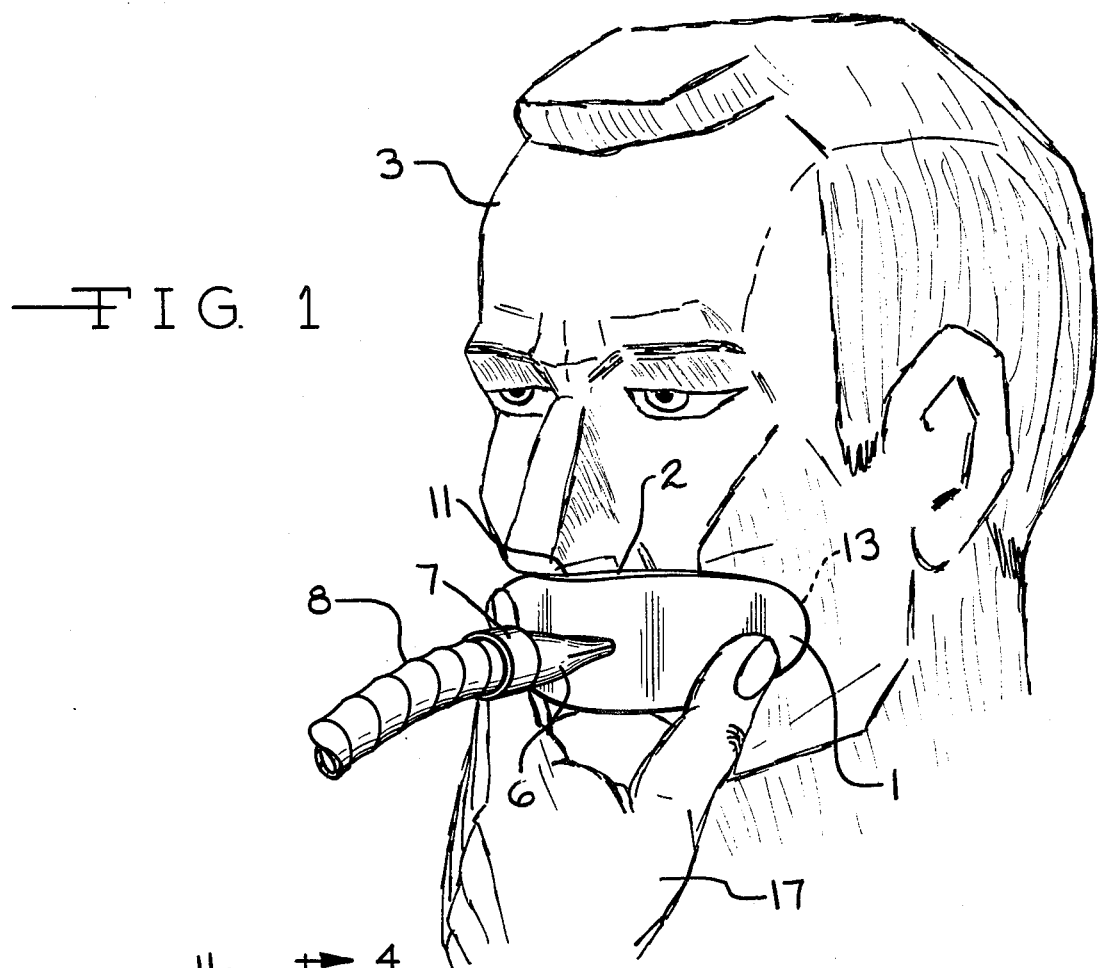
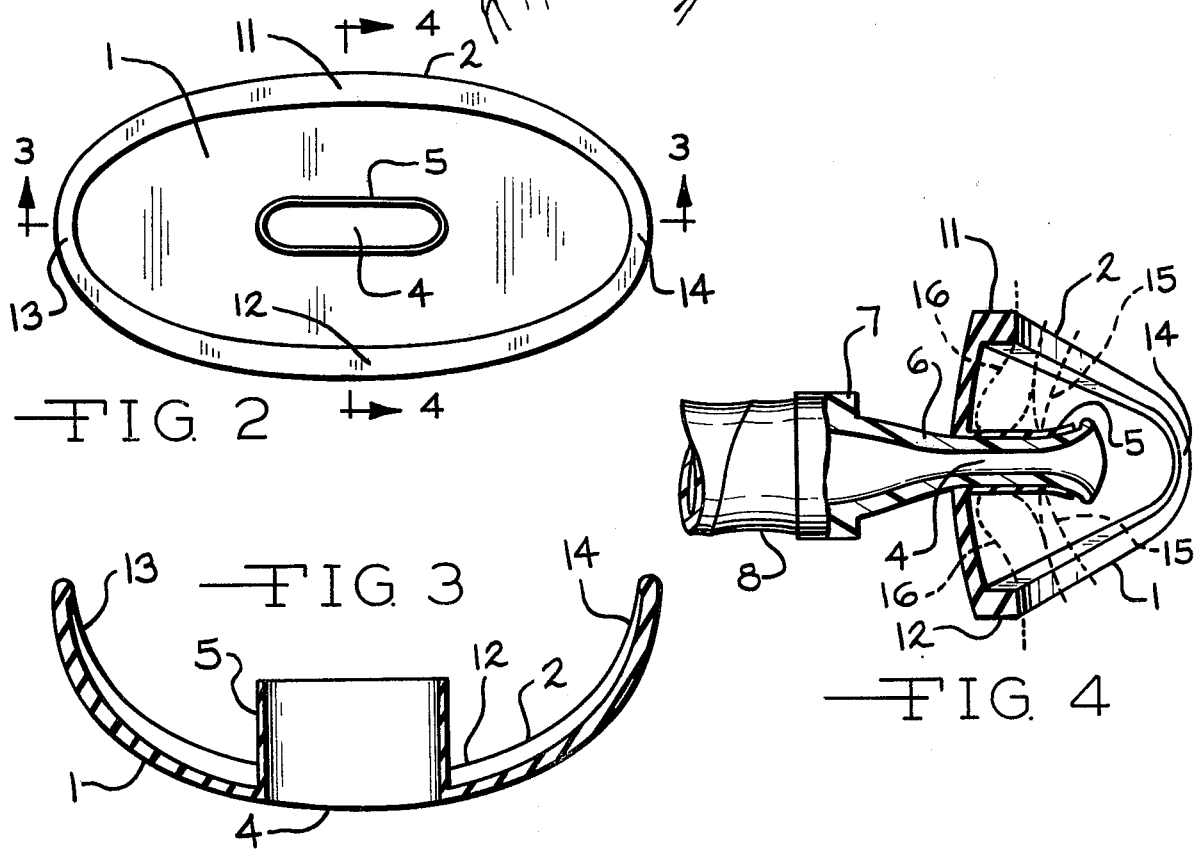

RESPIRATORY MOUTHPIECE

BACKGROUND OF THE INVENTION

This invention relates to respiratory appliances for administering gas to patients, and more particularly to an improved respiratory mouthpiece.

An object of the invention is to provide an inexpensively produced, efficient, disposable mouthpiece for a respiratory appliance.

Another object is to provide a mouthpice which is a one-piece integral unit which can quickly and easily be applied or removed in sealing condition around the end of a gas-administering tube to be inserted into the mouth.

Another object of the invention is to provide a mouthpiece which will provide an efficient seal against the passage of air when applied to the differing contours of upper and lower tooth or gum sections between nose and chin of various individuals, having regard to the fact that they may recede or jut, be relatively flat or more sharply rounded, be with or without teeth, or otherwise differ substantially. At the same time, it is desired to provide contours which can provide an efficient seal against the passage of gas along the relatively flat and soft cheek sections of the face at each side end of the mouthpiece.

Another object is to provide a design which is comfortable and induces acceptance from the patient.

Another object is to provide a mouthpiece which will provide an efficient seal against the passage of gas when applied to an unconscious patient or one unable through his or her own efforts to retain the mouthpiece in operative position.

Another object is to provide a mouthpiece which is free of recesses, undercuts or cuffs which would tend to retain saliva or mucous.

A further object is to provide a flexible mouthpiece of sufficient stiffness to avoid the use of metal supports or other added devices for retaining operative condition.

In use today is a respiratory mouthpiece shown in Bennett U.S. Pat. No. 2,857,911. As there shown, the mouthpiece has an in-curved cuff around the entire periphery of the mouthpiece which provides a recessed cavity or cup-like section, tending to retain mucous or saliva. Such a cuff also requires an added metal pressure plate for holding the cuff in operative position. It is also provided with a neck strap which has been found to be unnecessary and in many cases undesirable, particularly in cases where the patient wishes suddenly to cough or expectorate or in cases of patients unable to cooperate through being in a coma or too weak to operate the device through his or her own efforts. This device also is more expensive to produce, both in view of the multiple parts required, as well as the design of the mouthpiece with an in-curved section of the cuff and the method and apparatus for its production. Such a device is generally not intended to be disposable because of its cost, and therefore must be cleaned which is more difficult with the in-curved section of the cuff and several parts which require sterilization and possibly repackaging for reuse. Using a cuff, the material must be sufficiently soft to create a seal when pressed against the face, but such softness requires the metal pressure plate to provide sufficient stiffness when the mouthpiece is pressed to the face to form a seal against the mouth.

BRIEF DESCRIPTION OF THE DRAWINGS

FIG. 1 is a perspective view of the invention shown in operation on a patient;

FIG. 2 is an elevational back view of the mouthpiece of the invention;

FIG. 3 is a sectional side view of the mouthpiece; and

FIG. 4 is a sectional plan view of the mouthpiece.

DESCRIPTION OF THE PREFERRED EMBODIMENT

As shown in the drawings, the mouthpiece comprises an ovate face plate 1, curved essentially cylindrically, preferably with a radius of curvature of approximately 1¾ inches, and a wall thickness of about 0.06 inches for suitable stiffness and flexibility when made of flexible material described more fully below. The ovate shape includes within its meaning a substantially lenticular shpae. The face plate 1 may also curve from top to bottom in the same concave direction as shown in FIG. 4. An integral ridge 2 extends inwardly along the periphery of the concave side of the face plate to project inwardly against the outer skin surfaces, above and below the mouth and on the cheeks of a patient 3.

The center of the face plate 1 has an opening 4 defined by an inwardly extending tube 5 also integral with the face plate. The tube 5 is substantially flat at the top and bottom so as to form an elongated oval cross-section and facilitate its introduction into the mouth between the teeth 15, and permit the upper and lower lips 16 to easily encircle the tube 5 and form a seal when the patient closes his or her mouth around the tube 5. The mouthpiece 1 is made of flexible elastomeric material and thus is capable of being applied snugly by pushing or pulling over the end of a mouthpiece holder 6 shown in FIG. 3 of a rigid plastic or similar material. The mouthpiece holder 6 has a fitting 7 at its oppoiste ends for easy connection with a flexible tube 8 which communicates with a gas deliver apparatus for respiratory therapy. This may be an intermittent positive pressure breathing apparatus (not shown) well known in the art. This provides positive gaseous pressure for inhalation until back pressure is built up sufficiently by the patient to cause the inward pressure to terminate and enable the patient to exhale through the tube sufficiently before pressure is again applied by the breathing apparatus.

The upper and lower center sections, 11 and 12, respectively, of the ridge 2, are about 0.19 inches wide at their base and have straight parallel or tapering sides with a rounded top, or may be arcuate in cross-section as to avoid undercuts or recesses which may tend to hold mucous or saliva, and make it more difficult to remove the mouth piece from a mold when being produced. The center sections 11 and 12, of the ridge 2 have a height of about 0.19 inches, sufficient to form a seal when pressed inwardly against the upper and lower outer surfaces of the mouth beneath the nose and above or against the chin, respectively. The heights and widths of the ridge at these center sections are greater than the thickness of the face plate 1. The ridge 2 tapers to the extremities 13 and 14 so as to have a height and width considerably less than that in the center sections 11 and 12. At these extremities the ridge may have a height of 0.045 inches above the face plate; that is, no greater than or less than the thickness of the face plate itself. These extremities are adpted to press comfortably against the flatter regions of the cheeks and are sufficient to provide the necessary seal against the movement of air from or into the mouthpiece. The ridge in the center sections 11 and 12 are of sufficient height to conform to and provide a seal for varying shapes and mouth contours of different patients, whether jutting or receding, sharply curved or more rounded, and with or without the benefit of teeth, thus providing a seal of universal application. On the other hand, the ridge at the extremity is lessened to provide maximum comfort and provide surface contact against the flatter, softer tissues of the cheeks.

The material from which the mouthpiece is made is an elastomer of sufficient stiffness combined with sufficient flexibility to cause the ridge 2 to press gently into the outer surfaces of the skin around the mouth and provide a seal against the pressures of air from the respiratory apparatus. The material can be a vulcanized rubber and is preferably a thermoplastic elastomer. A preferred form is produced by Shell Oil Company and sold as "Kraton" thermoplastic rubber. A preferable grade is Kraton 2104 having a Shore hardness of 43 although Shore hardnesses between 38 and 55 can also be used. Shore hardnesses of 72 and 73 tend to have excessive hardness and stiffness, and Shore hardnesses below 38 tend to be too soft and not have sufficient stiffness to cause the ridge to press against the flesh of the patient efficiently and without discomfort.

Kraton rubbers are resilient materials which combine the properties of vulcanized elastomers and the processing advantages of thermoplastic. These versatile products are block copolymers of styrene and butadiene which may be fabricated into commercial products using standard thermoplastic processing equipment. Like all thermoplastics, they form free-flowing melts when subjected to heat and pressure and on cooling Kraton rubbers harden to give articles conforming to the mold or die-shape. At this point, the resulting product has physical properties which are essentially indistinguishable from vulcanized elastomers. Full tensile strength is achieved immediately after the molded parts cool. The material is injected under pressure into the mold at about 3,000 pounds per square inch pressure. It then cools and hardens and can be stripped out of the mold very easily. The mouthpiece ridge 2 has no undercut and therefore can be removed more easily directly from the mold.

In operation, the mouthpiece is fitted on the tube section 5 and the patient himself or herself, or a therapist or assistant inserts the tube 5 into the mouth and holds with his hand 17 the inner surface of the face plate closely against the mouth, thus gently pressing the ridge sections 11 and 12 against the upper and lower portions of the mouth and the ridge section 13 and 14 against the cheeks. If the patient is conscious and cooperative he or she will close the teeth 15 and lips 16 gently around the tube section 5 to provide a normal seal against the escape of gas and permit the incoming gases to be inhaled. In the event the patient is unconscious or otherwise unable to cooperate, and a seal cannot be obtained in an ordinary manner around the tube 5, the seal can be efficiently effected by the face plate and ridge 2 as it is held in place by the attendant. In the even of sudden need to cough or expectorate, the mouthpiece is swiftly removed and saliva and mucous easily eliminated.

When the face plate is pressed inwardly around the mouth, the concave shape tends to straighten and when this occurs in the center sections of the face plate, the center sections 11 and 12 of the ridge tend to bend outwardly and provide a more effective gaseous seal. The ridge of lower height at the end sections 13 and 14 cooperates and assists in the effectiveness of the seal at not only the center sections but also against the cheeks of the patient.

The dimensions and material specifications of the preferred embodiment may be adjusted by one skilled in the art without departing from the invention or losing the main recited advantages.

We claim:
1. A flexible, resilient respiratory mouthpiece for a therapeutic breathing apparatus comprising
   a. a substantially ovate, concave face plate,
   b. a ridge along the periphery of the concave side of said face plate having a height above the face plate greater than the wall thickness of the face plate in the regions across the shorter diameter of the face plate, and a height above the face plate no greater than the said wall thickness in the regions of the ovate extremities of the face plate and
   c. a tube defining an elongated opening in the center of the face plate and extending inwardly on the concave side of the face plate, adapted to fit over a mouthpiece holder of a breathing apparatus;
   d. the mouthpiece being a one piece integral molding of an elastomeric material having sufficient stiffness and flexibility to provide a seal against air pressure entering the mouth from the breathing apparatus when the ridge is pressed inwardly against the outer surfaces around a patient's mouth.
2. The mouthpiece as defined in claim 1 in which the sides of the ridge are free of undercuts along its length.
3. The mouthpiece as defined in claim 1 in which the sides of the ridge lie between parallel surfaces extending at right angles to the face plate along the length of the ridge so as to be free of undercuts along its length.
4. The mouthpiece as defined in claim 1 made of flexible, elastomeric material having a Shore hardness between 38 and 55.
5. The mouthpiece as defined in claim 1 made of thermoplastic block copolymer of styrene and butadiene having a Shore hardness between 38 and 55.

* * * * *